United States Patent
Vrána et al.

(10) Patent No.: US 8,895,059 B2
(45) Date of Patent: Nov. 25, 2014

(54) REDUCTION OF CROSS-LINKING GELATIN IN GELATIN CAPSULES

(75) Inventors: Aleš Vrána, Opava (CZ); Tomáš Andrýsek, Branka u Opavy (CZ); Alexandr Jegorov, Dobra Voda (CZ); Richard Szrajber, Opava (CZ)

(73) Assignee: Ivax Pharmaceuticals S.R.O., Opova (CZ)

( * ) Notice: Subject to any disclaimer, the term of this patent is extended or adjusted under 35 U.S.C. 154(b) by 2687 days.

(21) Appl. No.: 10/516,904

(22) PCT Filed: Jun. 5, 2003

(86) PCT No.: PCT/US03/17620
§ 371 (c)(1),
(2), (4) Date: Nov. 29, 2007

(87) PCT Pub. No.: WO03/103582
PCT Pub. Date: Dec. 18, 2003

(65) Prior Publication Data
US 2011/0097398 A1    Apr. 28, 2011

Related U.S. Application Data

(60) Provisional application No. 60/386,115, filed on Jun. 5, 2002.

(51) Int. Cl.
*A61K 9/48* (2006.01)
*A61K 31/355* (2006.01)
*A61K 47/18* (2006.01)

(52) U.S. Cl.
CPC ............. *A61K 9/4808* (2013.01); *A61K 9/4825* (2013.01); *A61K 9/4858* (2013.01); *A61K 31/355* (2013.01); *A61K 47/183* (2013.01)
USPC .......................................... 424/452; 424/456

(58) Field of Classification Search
None
See application file for complete search history.

(56) References Cited

U.S. PATENT DOCUMENTS

| | | | |
|---|---|---|---|
| 2,467,715 A | 4/1949 | White | |
| 2,519,487 A | 8/1950 | Macek et al. | |

(Continued)

FOREIGN PATENT DOCUMENTS

| | | | |
|---|---|---|---|
| DE | 225 426 A1 | 7/1985 | |
| DE | 295 765 A5 | 11/1991 | |

(Continued)

OTHER PUBLICATIONS

English translation of JP 63215641 (Sep. 1988) 14 pages.*
Cyclosporin-A (product sheet) Sigma (retrieved online Mar. 8, 2012) pp. 1-2.*

(Continued)

*Primary Examiner* — Bethany Barham
(74) *Attorney, Agent, or Firm* — Kenyon & Kenyon LLP (57) ABSTRACT

The invention relates to compositions and methods for reducing cross-linking in the gelatin shell of gelatin capsules by incorporation of free amino acid into the capsule shell and by inclusion of an ester of carboxylic acid either into the capsule filling, and/or into the capsule shell and/or into the lubrication agent, or in combinations thereof. Described are soft gelatin capsules characterized by improved stability as compared with gelatin capsules that do not contain amino acid in the shell and carboxylic acid ester in the filling, shell or in the lubrication agent, or in combinations thereof.

19 Claims, 3 Drawing Sheets

Dependance of Gelatin-related Absorbance on Dissolving Time of Gelatin Discs

(56) References Cited

U.S. PATENT DOCUMENTS

| | | | |
|---|---|---|---|
| 3,456,051 | A | 7/1969 | Mima et al. |
| 4,255,413 | A | 3/1981 | Rattie et al. |
| 5,186,944 | A | 2/1993 | Ishii et al. |
| 5,405,616 | A | 4/1995 | Wunderlich et al. |
| 5,620,704 | A | 4/1997 | Cade et al. |
| 5,897,876 | A | 4/1999 | Rudnic et al. |
| 6,046,163 | A * | 4/2000 | Stuchlik et al. .............. 514/20.5 |
| 6,090,414 | A * | 7/2000 | Passwater et al. ............ 424/702 |
| 6,319,943 | B1 * | 11/2001 | Joshi et al. .................... 514/449 |

FOREIGN PATENT DOCUMENTS

| | | |
|---|---|---|
| FR | 2617047 | 12/1988 |
| JP | 63-215641 * | 9/1988 |
| JP | 6321541 | 9/1988 |
| JP | 6420078 | 1/1989 |
| JP | 200002682 | 1/2000 |
| WO | 96/14365 A2 | 5/1996 |
| WO | WO 97/33568 | 9/1997 |
| WO | 0234238 A2 | 5/2002 |
| WO | 2004010972 | 2/2004 |
| WO | 2004010973 | 2/2004 |
| WO | 2004010974 | 2/2004 |
| WO | 2004022032 | 3/2004 |

OTHER PUBLICATIONS

"Product Information Miglyol® 810, 812, 818, 829, 840 Neutral Oil for Pharmaceuticals and Cosmetics" from Sasol Germany GmbH (Sep. 2004) pp. 1-7 (http://abstracts.aapspharmaceutica.com/expoaaps07/Data/EC/Event/Exhibitors/263/cb63fb76-28f4-4948-a6d0-ae249dae9c30.pdf).*

Supplementary European Search Report, EP 03731548, dated Nov. 17, 2010.

Horn and Jimerson, Capsules, Soft, Encyclopedia of Pharmaceutical Technology, vol. 2, Swabrick and Boylan (Eds), Marcel Dekker, New York and Basel, 269-284 (1990).

Lachmann, Theory and Practice of Industrial Pharmacy, 2nd Ed. Lea and Febiger, Philadelphia (1986).

York, J. Pharm. Pharmacol. 33:269 (1981).

Carstensen and Rhodes (Drug Dev. Ind. Pharm. 19(20):2709 (1993).

Bottom, et al., (J. of Pharm. Sci. 86(9):1057 (1997).

Chafetz, et al., J. Pharm. Sci. 73:1186 (1984).

Dey, et al., Pharm. Res. 10(9)1295 (1993).

Digenis, et. al., J. Pharm. Sci. 83(7):915 (1994).

Murthy, et al., Pharm. Tech. 13(6):53 (1989).

Murthy et al., Pharm. Tech. 72 (1989).

Ptachinski, Robert J., et al., "Stability and Availablity of Cyclosporine Stored in Plastic Syringes", American Journal of Hospital Pharmacy, vol. 43, pp. 692-694, Mar. 1986.

* cited by examiner

REDUCTION OF CROSS-LINKING GELATIN IN GELATIN CAPSULES

CROSS REFERENCE TO RELATED APPLICATION

This application is a U.S. national phase of international application No. PCT/US2003/17620, filed Jun. 5, 2003, which claims the benefit of U.S. Provisional Application No. 60/386,115, filed Jun. 5, 2002.

BACKGROUND OF THE INVENTION

1. Field of the Invention

The invention relates to compositions and methods for reducing cross-linking in the gelatin shell of gelatin capsules by incorporation of free amino acid into the capsule shell and by inclusion of an ester of carboxylic acid either into the capsule filling, and/or into the capsule shell and/or into the lubrication agent, or in combinations thereof. Described are soft gelatin capsules characterized by improved stability as compared with gelatin capsules that do not contain amino acid in the shell and carboxylic acid ester in the filling, shell or in the lubrication agent, or in combinations thereof.

2. Summary of the Related Art

Gelatin capsules, commonly used as a pharmaceutical dosage form or as food supplements, consist of a gelatin shell surrounding a core filled with the composition being delivered. Gelatin capsules and methods of making the same are well known and described in the general pharmacological literature. Gel capsules may be hard (filled with solid or semi-solid fill) formed by two halves joined to create a shell capsule, or a soft (filled with a liquid or semi-liquid fill) formed by a single gelatin shell. Caplets (sometimes also referred to as gel capsules) are modified tablets covered by gelatin shell.

Soft-gelatin capsules are produced by injecting a liquid or a semi-liquid fill between two gelatin strips, either by discontinuous formation or by continuous formation (i.e., rotary-die process). During the manufacturing process, both gelatin gel strips have to be lubricated by a suitable lubricant in order to avoid early sticking to machine parts or to each other. Suitable lubricant agents commonly used in the art include mineral oils (e.g., paraffin oil), synthetic oils (e.g., silicone oil) or vegetable oils (e.g., coconut oil and corn oil).

Liquid or semi-liquid fills for soft-gelatin gel capsules are divided into two basic groups according to their miscibility with water (see, Horn and Jimerson, *Capsules, Soft*, In: *Encyclopedia of Pharmaceutical Technology*, Vol. 2, Swabrick and Boylan (Eds), Marcel Dekker, New York and Basel, 269-284, 1990; and Lachmann, *Theory and Practice of Industrial Pharmacy*, $2^{nd}$ Ed. Lea and Febiger, Philadelphia, 1986). In a first group are hydrophobic fills capsules (e.g., vegetable and aromatic oils, aromatic and aliphatic hydrocarbons, chlorohydrocarbons, ethers, esters, alcohols and high molecular organic adds), whereas in a second group are hydrophilic fills capsules (e.g., polyethyleneglycols and non-ionogenic surfacial active material—surfactants).

After encapsulation of hydrophobic fills into gelatin gel, excess water leaves the gel and enters the fill. The excess water is almost completely resorbed by the gelatin shell of the capsule during the drying process, until equilibrium with the surroundings is achieved. Conversely, hydrophilic fills are able to absorb a certain amount of water, which can enter the fill after encapsulation. The resorption process is more difficult for these fills and equilibrium achievement is conditioned by the HLB (hydrophilic to lipophilic balance) value and absorption hysteresis curve for gelatin shells of concrete composition (York, *J. Pharm. Pharmacol.* 33:269 (1981)).

A third group of compounds and compositions, which are not suitable for incorporation in a gelatin capsule includes: water and aqueous solutions, low molecular weight and water-soluble volatile organic substances (e.g., organic acids, alcohols, ketones, aldehydes, amines and esters). Besides their principle unsuitability for encapsulation due to dissolution-related impairment of the gelatin gel, some of these compounds can have deteriorating effect on the gelatin shell even if they are present in trace amounts. These compounds have been found to promote gelatin cross-linking (i.e., the formation of covalent chemical bonds across the polypeptide chains of gelatin) in the gelatin shell resulting in an insoluble polymer structure. Cross-linking may also arise during storage of gelatin capsules giving rise to a molecular (net-like) structure of gelatin, which is almost insoluble or poorly dissoluble in water.

It is also known that gelatin cross-linking in the shell of the capsules is promoted by use of certain chemical compounds in the fill of capsules and can arise in the course of aging of the capsules or after stress conditions. The formation of such a molecular (net-like) structure of gelatin results in worsened disintegration profile of the capsules resulting in a delayed release of pharmaceutically active substances contained in the capsule.

Factors Affecting Dissolution Test of Soft Gelatin Capsules with Pharmaceutically Active Substances The employment of gelatin capsules as an oral delivery means is well known in the pharmaceutical arts. In pharmaceutical applications, soft gelatin capsules are especially suitable for oral administration of lipophilic active substances. However, once the cross-linking of the gelatin occurs, the gelatin shell becomes less soluble in an aqueous medium, especially in an acidified water medium. The cross-linking delays the disintegration of the gelatin shell, which subsequently delays the dissolution of the inner content of the capsule as compared with a similar capsule not exposed to long time storage or stress-conditions which promote cross-linking.

Therefore, it is necessary when the gelatin capsule contains a component which promotes cross-linking in the gelatin shell to prepare a formulation which will not induce delayed disintegration and/or delayed dissolution of the inner content of the capsule following storage or after exposure to stress conditions.

The shells of both hard and soft gelatin capsules are susceptible to cross-linking. Cross-linking has been demonstrated by a prolongation of the dissolution time and release of drug substance. The delay is attributed to only partial dissolution of the gelatin shell (in case of soft gelatin capsules, the dissolved part is the outer layer of shell). In some instances, the inner layer of the gelatin shell forms a thin film, called a pellicle, which remains intact and envelopes the inner volume of the capsules. This effect is described by Carstensen and Rhodes (*Drug Dev. Ind. Pharm.* 19(20):2709 (1993)) or Bottom, et al., (*J. of Pharm. Sci.* 86(9):1057 (1997)).

Considering relatively small intensity of mixing in dissolution apparatus, the rupture of gelatin shell containing the pellicle is worsened and delayed as well and it is the cause of high variability of results of the dissolution test.

There are presently two basic methods described in the literature addressing the dissolution problems of soft gelatin capsules. These methods include (a) demonstrating that the altered dissolution profiles obtained from cross-linked gelatin capsules is a laboratory phenomenon by utilizing in vivo bioequivalence and/or clinical studies which attempt to demonstrate that actual biological availability of test agents are not negatively affected by the cross-linking; and (b) elimination of the causes of cross-linking, namely (i) elimination of physical conditions, which promote the cross-linking, (ii) elimination of substances, which promote the cross-linking (cross-linking promoters), (iii) addition of cross-linking inhibitors (where the most effective action is concurrent combination of these precautions).

In Vivo Studies with Capsules Affected with Cross-Linking

Although the changes of bioavailability of a drug during the shelf-life are always accompanied with the changes in dissolution characteristics and/or are even indicated by them in advance, it is not true vice versa—i.e., the changes in dissolution characteristics do not always necessarily indicate the deterioration of bioavailability.

Chafetz, et al., J. Pharm. Sci. 73:1186 (1984) showed a typical example in which the pellicle formed by gelatin cross-linking did not rupture in vitro, but always disintegrated in the patient's stomach. Similar observations showing that gelatin cross-linking has greater impact on the result of the in vitro dissolution test rather than on the in vivo bioavailability of a drug have been reported. (See e.g., Dey, et at, Pharm. Res. 10(9):1295 (1993), Digenis, et. al., J. Pharm. Sci. 83(7):915 (1994), or Murthy, et al., Pharm. Tech. 13:(6):53 (1989)). Special importance among these studies belongs to the work of Digenis, et al.

While it appears that gelatin cross-linking has far more greater impact on the results of in vitro dissolution tests rather than on in vivo bioavailability, it is still prudent to utilize such formulations of the inner fillings of the gelatin capsules which minimize cross-linking in the gelatin shell and which therefore minimize the effects of time or stress conditions on the dissolution profile of the gelatin capsules. This may be especially important in a case of accelerated stability studies in which the capsules are stressed with enhanced temperature and relative humidity. The reason is that the results of accelerated stability studies are often used for drug registration purposes, and that the dissolution test is often required as one of the stability-indicating methods.

Elimination of the Causes of Cross-Linking

Cross-linking of the gelatin capsules may be promoted or accelerated by physical conditions or chemical substances.

Physical conditions which promote or accelerate cross-linking include: (a) the combination of elevated temperature and humidity (Murthy et al., Pharm. Tech. 72 (1989)), (b) heating (critical temperature is between 37-40° C.) (Hakata et al., Chem. & Pharm. Bull. 42(7):1496 (1994)), (c) dehydration as a result of heat treatment (Welz and Ofner, J. Pharm. Sci. 81(1):85 (1992)), (d) speed of drying (Reich et al., Pharm. Industry 57 (1995)), or (e) UV radiation.

Chemical substances which activate, facilitate or force cross-linking include among others glucose, aldehydes (glutaraldehyde, formaldehyde, glyceraldehyde), peroxides (hydrogenperoxide), epoxides (1,3-butadiene diepoxide), benzene, sulfonic acid, or guanidine hydrochloride. Metal salts react with gelatin also and thus by complexation with the carboxylate groups (chromium salts, zirconium, aluminium). Cross-linking reaction of gelatin is intentionally used in photographic industry for hardening of gelatin gels. A great deal of information about this subject is contained in books (Clark, R. C. and Courts, A., "The Chemical Reactivity of Gelatin" in *The Science and Technology of Gelatin*, (ed.) A. G. Ward and A. Courts, Academic Press, (1977); Chonan, Y. et at, "The effects of Chemical Modification on the Physical Properties of Gelatin" in *Photographic Binders, 2nd Edition*, (ed.) H-Irie et al., Published by the Research Group of Photographic Binders in Japan (1990)).

Cross-linking of the gelatin in gelatin capsules is inhibited or reduced by chemical substances, which include among others: aminoacids (glycine, lysine), carboxylic acids (citric acid), semicarbazide, hydroxylamine hydrochloride, piperazide, pyridine, pentamethylene imine, glycerine, or p-aminobenzoic acid.

It is known that gelatin cross-linking in gelatin capsules can be reduced or avoided if the amount of amino-groups available along the molecular chain of the gelatin is reduced, either by masking through covalent bonds with suitable masking agents or by employment of competitive agents containing an abundance of free amino-groups.

A representative masking agent often used is succinic acid, because the two carboxyl groups of this organic acid enable both the reaction of one carboxyl group with an accessible amino-group on the molecular chain of the gelatin and, concurrently providing steric prevention of access of the cross-linking agent. The process where the gelatin is modified by covalent binding of its molecules with succinic acid is called succination (succinization). A disadvantage of this approach results from the fact that the gelatin gels prepared from a modified (succinated) gelatin are characterized by high permeation and as such they are inappropriate for encapsulation of fillings which contain ethanol, propylene glycol or other volatile or migratable ingredients. Besides this, succinated gelatins are still susceptible to cross-linking when complexation agents such as metal salts are the cross-linking promoters.

Free monomeric amino acid is often used as a competition agent, for example glycine or lysine, whose free amino group competes with accessible amino groups on the molecular chain of the gelatin during its reaction with cross-linking agent.

Influence of Glycine on Cross-Linking

The inhibitory effect of glycine on cross-linking is more intensive when free and accessible carboxyl groups are concurrently present. See, for example, Adesunloye and Stach (Drug. Dev. Industrial Pharmacy, 1998).

It appears that glycine prevents cross-linking in both alcohol and non alcoholic formulations for gelatin capsules (unpublished observations of inventors). Glycine is currently used in pharmaceutical preparations, where dimethyl isosorbide is used as a solvent. A glycine concentration of around 0.5% is used for prevention of cross-linking.

Pharmaceutical Acceptance of Glycine Usage in the Shell of Soft Gelatin Capsules—Practical Feasibility There are no limitations for the use of glycine in capsules as mentioned in the list of adjuvants permitted by United States Food and Drug Administration's (FDA) *Inactive Ingredient Guide* (IIG) from year 1996. However, from the specifications for tablets, oral powders, food products or beverages, the following supporting data can be obtained:

| | Concentration |
|---|---|
| Food and drinks (CFR Ch. I (Apr. 1, 2000 Edition)) | |
| auxiliary masking substance (glycine) | 0.2% in final drink |
| Pharmaceuticals (IIG) | |
| Intramuscular injections | (limits unpublished) |
| freeze-dry powder for intramuscular injection solution | (limits unpublished) |
| Capsules, oral | (limit unpublished) |
| Powder for reconstitution solution, oral | (2.1%) |
| Oral solution | (limits unpublished) |
| Oral tablets | (8.X mg-163.31 mg) |

|                                                          | Concentration      |
|----------------------------------------------------------|--------------------|
| Oral tablets (immediate/comp. release), uncoated         | (100 mg-200 mg)    |
| Rectal solution                                          | (limits unpublished) |
| Powder for reconstitution of solution, subcutaneous      | (limits unpublished) |

The patent literature discloses glycine contents between 0.1 to 25.0%, most preferably of 0.2 to 5%, related to a fresh gelatin gel. The glycine concentrations presented below describe levels reported for use in some common dosage forms. Amounts in common use include: 1.08 mg per 1 capsule (size 5 oval), 2.52 mg per 1 capsule (size 11 oblong), and 3.94 mg per 1 capsule (size 20 oblongs).

It is also known, that the effect of competition agents (free amino acid containing moieties) can be further intensified (potentiated) by the concurrent use of a substance with a free carboxyl group, generally an organic acid. For organic acids, the monomeric lower carboxyl acid is often used, as for example citric acid. However, this approach has so far been used only in hard gelatin capsules, containing powdered or semi-solid dry fills. It has not been possible to apply this method to soft gelatin capsules, where the dominant lipophilic character of fill components did not allow for the use of lower monomeric organic acids, which are soluble in aqueous and hydrophilic media and insoluble in oily or lipophilic media.

In soft gelatin capsules production, a combination of the above mentioned approaches is used so that the succination of polymeric gelatin chain is performed by reaction with succinic acid anhydride. Concurrently, glycine or lysine is added as a free amino-acid into the gel composition.

However, to date several disadvantages have accompanied this approach. The first drawback comes from the fact that the product formed as a result of the reaction of gelatin with succinic acid anhydride has not been recognized as an acceptable auxiliary pharmaceutical compound (excipients).

The second drawback is caused by the high permeability of gelatin gels prepared from succinated gelatin. This feature makes them unsuitable for encapsulation of fillings containing ethanol, propylene glycol or other volatile or migratable components.

RELATED PATENTS

Special precautions leading to suppression of gel solidification of gels of animal origin (gelatin gels) promoted by reducing sugars was described for the first time in the U.S. Pat. No. 2,467,715. This patent describes the utilization of various ammonium salts (ammonium sulfate, ammonium phosphate, ammonium acetate, ammonium chloride, ammonium nitrate and ammonium thiocyanate). This case was directed to formed gelatin gels and not to the capsules containing fill, in which the water soluble reducing sugars were incorporated into the gel. Additionally described was the use of the agents (ammonium salts) for blocking hardening and cross-linking of the gel by action of these sugars. Finally, the amino acids disclosed were not used as compounds for blocking the hardening (cross-linking) of the gel.

A similar procedure, i.e., the use of ammonium salts (ammonium sulfate, ammonium sulfite, ammonium bisulfate, ammonium acetate and ammonium hydroxide), in connection with filled gelatin capsules with deteriorated disintegration as a consequence of aldehyde reaction, was described in French Patent FR2617047. The amino acids were not described as compounds for inhibiting the cross-linking.

U.S. Pat. No. 4,255,413 discloses improvement of the dissolution of soft gelatin capsules, in which the fill contains a composite formulation of poorly soluble active substances and surfactant. However, this invention maintains the use of surfactants and carbonated or bicarbonated salts, for example calcium carbonate, ammonium, sodium and potassium, in the fill.

Patent Application DD 225 426 A1 describes the use of nicotinamide, methylacetamide and urea for stabilization of gelatin gels. However, as used, the term stabilization in this case referred to the stabilization of fresh gelatin compositions whose workability into forms (i.e., soft gelatin capsules) is time constrained by the progressive aging and degradation of fresh gelatin gel which occurs within a few hours after its preparation.

Japanese Patent Application JP 6321541 describes the use of amino acids for the first time, in particular glycine, lysine and aspartic acid, for the suppression of insolubility of caramel containing soft gelatin. However, the benefits of the mentioned solution are described only for gelatin capsules containing caramel as a part of the gelatin shell, namely for such fills which must be protected from light (tocopherol, vitamins A, vitamins D, nifedipine, indomethacine, vitamins K).

The use of glycine in connection with gelatin is further described in U.S. Pat. No. 5,405,616. However, the disclosure relates to dry cryopellet production, formed by two hydrophilic gel matrices. The base for the first gel matrix is a polymer composed of amino acids (peptide) and the base for the second gel matrix is a polymer composed of sugars (polysaccharide) or polymer composed of amino acids (peptide) or from acrylate or methacrylate (polyacrylate, polymethacrylate), or simple sugar or simple amino acid, as for example glycine.

A method for improving soft gelatin capsule stability under the influences of enhanced temperature, humidity or aldehydes, is described in U.S. Pat. No. 5,620,704. The method consists in the incorporation of an additive or mixture of additives into the gelatin gel before encapsulation. The preferred additives are glutamic acid, tryptophan and nitrilotrismethylene phosphonic acid. The claims further include ammonium hydrogencarbonate and carbonate, ammonium sulfur dioxide and hydrogendioxide, ammonium phosphate and hydrogenphosphate, an ammonium thiocyanate, as well as sodium, potassium, lithium, calcium and magnesium sulfates and chlorides, ferrous and ferric chloride and sulfate, aspartic acid and asparagine, lysine, arginine, guanidine, urea, citric acid, ascorbic acid and ethylenediamintetraacetic acid (EDTA). The claims do not include glycine. Synergism of cross-linking inhibitor (as for example the carrier of amino-group) and substances amplifying this inhibition (as for example the carrier of carboxyl group) is not used. It is also evident from the examples that when the combination of above mentioned substances is used, it is always done solely by their incorporation into the formulation of the gelatin mixture only.

Japanese Patent Application JP 01020078A further describes preparation of soft gelatin capsules with hydrophilic fills.

The Patent Application DD 295 765 A5 discloses the preparation of freeze-dried pharmaceutical formulations with cyclosporin, where the dispersion of cyclosporin is incorporated into a hydrophilic gel. The matrix here is formed similarly to that from U.S. Pat. No. 5,405,616, using polymer composed of amino acids (peptide) or polymer composed of sugars (polysaccharide) or polymer composed of amino acids (peptide) or from acrylate or methacrylate (polyacrylate, polymethacrylate), or simple sugar or simple amino-acid, as for example glycine. The pharmaceutical composition is filled into tablets, capsules, or pellets only after freeze-drying. The disclosure does not teach the preparation of gelatin capsules displaying improved disintegration and dissolution characteristics as a result of an inhibition of the gelatin cross-linking.

Utilization of the synergic effect of a concurrent use of a cross-linking inhibitor (as for example a carrier of amino group) and a compound amplifying this inhibition effect (as for example a carrier of a carboxy group) was first described in WO 97/33568. Glycine was used as an amino acid cross-linking inhibitor and citric acid used as a compound for amplifying this inhibitory effect (inhibition enhancer). Contrary to U.S. Pat. No. 5,405,616, where citric acid was used as a component of the gelatin mixture and incorporated in the gel, WO 97/33568 describes such a use where both of these compounds are used as components of the formulation of the inner fill of a gelatin capsule. Finally, it appears from the detailed description of the invention that the inventors considered their solution applicable for hard gelatin capsules only which are filled with solid fillings in form of dry powder or granulate.

In a similar context, U.S. pre-issue publication number 2000/026282 A1 describes a method for the improvement of dissolution characteristics of hard gelatin capsules filled with solid fillings in the form of a powder or granulate, using glycine in the formulation of the filling of hard gelatin capsules.

Thus, to date the preparation of soft gelatin capsules having significantly reduced cross-linking in the capsule shell and displaying a significantly improved dissolution profile has been considered technically difficult or impossible, especially in those instances where the filling solution is of type 2 (described above) and consists in some part of hydrophilic or partially hydrophilic compounds miscible with water, (for example, polyethyleneglycols and non-ionogenic surfactants), and/or in the case when the filling solution contains compounds capable of migration into the soft gelatin capsule shell, (for example, lower alcohols (ethanol, ethylene glycol, propylene glycol), and/or in the case when the filling solution contains compounds which facilitate or promote migration of compounds other than water from the gelatin shell of the capsule into its fill. Furthermore, problems arise where no other known method for the prevention of gelatin cross-linking could be employed, as for example is the method of succination of the gelatin polymeric molecule.

SUMMARY OF THE INVENTION

The instant application overcomes many of the technical disadvantages of the currently available approaches based on the findings that the effect of gelatin cross-linking on the gelatin capsule, can be reduced or eliminated by the use of effective amount of moieties which prevent/reduce gel cross-linking. These findings are applicable to both hard and soft gelatin capsules containing hydrophilic and lipophilic fillings, without concomitantly increasing gel permeability for migratable components.

The inventors have identified suitable compounds and combination thereof which function as cross linking inhibitors and cross linking inhibitor-enhancers resulting in gelatin capsules with improved stability as compared to gelatin capsules which do not contain such moieties. The inhibitors and inhibitor-enhancers of the invention have been found to be effective not only by their simple concurrent addition into the formulation of the capsule filling, but also by their incorporation into the formulation of gelatin shell, or by their separate addition into the formulation of gelatin capsule shell and inclusion into the formulation of the capsule fill. It has also been found that the inhibitors and inhibitor-enhancers may be separately supplied into the formulation for gelatin capsule shell and/or into the formulation of capsule fill on one side and into, for example, lubrication oil for gelatin ribbons on the other side.

Hence, the instant invention provide in one aspect gelatin capsules comprising a fill and a gelatin shell containing amino-acid cross linking inhibitor, wherein the gel capsule also includes a cross-linking inhibitor enhancer. In some embodiments of the invention, the cross-linking inhibitor enhancer is a carboxylic acid ester.

Another aspect of the invention consists of methods for potentiating the action of a cross-linking inhibitor in a gelatin shell of a gelating capsule with a cross-linking inhibitor enhancer. In some embodiments described herein, cross-linking inhibitor enhancers are carboxylic acid esters.

BRIEF DESCRIPTION OF THE DRAWINGS

FIG. 2 overall shows a comparison of multiple samples of gelatin capsules with Cyclosporine as the active ingredient in the capsule fill, cross-linking inhibition enhancer in the fill and cross-linking inhibitor in the shell versus gelatin capsules with Cyclosporine as the active ingredient without a cross-linking inhibition enhancer in the fill and without a cross-linking inhibitor in the shell.

DETAILED DESCRIPTION OF THE INVENTION

The inventors have identified suitable compounds and combination thereof which function as cross-linking inhibitors and cross-linking inhibitor enhancers resulting in gelatin capsules with improved stability as compared to gelatin capsules which do not contain such moieties. The cross-linking inhibitors and inhibitor enhancers of the invention have been found to be effective not only by their simple concurrent addition into the formulation of gel capsule filling, but also by their incorporation into the formulation of gelatin shell, or by their separate addition into the formulation of gelatin capsule shell and inclusion into the formulation of the capsule fill. It has also been found that cross-linking inhibitors and inhibitor enhancers may be separately supplied into the formulation for gelatin capsule shell and/or into the formulation of capsule fill on one side and into, for example, lubrication oil for gelatin ribbons on the other side.

Hence, the instant invention provide in one aspect gelatin capsules comprising a fill and a gelatin shell containing amino-acid cross linking inhibitor, wherein the gel capsule also includes a cross-linking inhibitor enhancer. In some embodiments of the invention, the cross-linking inhibitor enhancer is a carboxylic acid ester.

Another aspect of the invention consists of methods for potentiating the action of a cross-linking inhibitor in a gelatin shell of a gelating capsule with a cross-linking inhibitor enhancer. In some embodiments, the cross-linking inhibitor and the cross-linking inhibitor enhancers result in a synergistic effect (i.e., the overall cross-linking reducing effect observed when using both is more than the sum of the reducing effect observed when using the inhibitor and the enhancers alone).

In some embodiments described herein, cross-linking inhibitor enhancers are carboxylic acid esters.

More specifically, the invention sets forth compositions and methods for reducing cross-linking in the gelatin shell of gelatin capsules by incorporation of free amino acid into the capsule shell and by inclusion of an ester of carboxylic acid either into the capsule filling and/or into the capsule shell and/or into the lubrication agent, or into combinations thereof. The fill is the second type fill, i.e. has such character that it contains water miscible liquids, e.g., polyethyleneglycols or non-ionogenic surface active compounds (surfactants), i.e. agents in general which are capable of bonding a portion of the water penetrating into a capsule fill after its encapsulation. At the same time, either the gelatin shell or the gelatin fill, or both parts, contains the agent(s) which enables, enhances or induces cross-linking. The method consists in the concurrent use of sufficiently active amount of two agents where one of the agents reduces cross-linking of the gelatin itself (an inhibitor of gelatin cross-linking) and the second one strengthens and potentiates this inhibitive effect (inhibition amplifier). The cross-linking inhibitor is incorporated into the composition of gelatin shell and the inhibition amplifier is contained, depending on the character of the fill, in either the capsule fill and/or gelatin shell and/or a lubricant used in the manufacture of capsules or in all the components of gelatin capsules simultaneously.

The technical and scientific terms as used herein have the meaning commonly understood by one of skill in the art to which the present invention pertains, unless defined otherwise. Reference is made herein to various methodologies and materials known to those of skill in the art. Standard reference works setting forth the general principles of pharmacology include *Goodman and Gilman's The Pharmacological Basis of Therapeutics*, 9$^{th}$ Ed. (McGraw Hill Companies Inc., New York, 1996). Standard reference works setting forth the general principles of pharmaceutical formulations include *Remington's Pharmaceutical Sciences*, 18$^{th}$ Ed., (Gennaro, Mack Publishing Co., Easton, Pa., 1990) and *Remington: The Science and Practice of Pharmacy* (Lippincott, Williams & Wilkins, 1995).

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

The manufacture of gelatin capsules is well known pharmaceutical technique. The gelatin capsules include every such dosage form or food supplement in which the fill material is packaged in a gelatin shell. Such capsules can be, for example, hard capsules filled with a solid or semi-solid fill and formed of two separate halves of shell which fit one another to form the finished shell of a capsule, or, soft capsules whose liquid or semi-liquid fill is encapsulated by one piece of gelatin shell, and possibly also so-called caplet, i.e., tablets covered in a gelatin shell.

Soft gelatin capsules are manufactured by conventional methods well known in the art such as by injecting a liquid, semi-liquid or paste-like fill between two lubricated gelatin ribbons in a rotary-die process of continual formation. Both ribbons of the gelatin gel must be lubricated with an appropriate lubricant in order to avoid premature sticking of the fresh gelatin gel to machinery or to each other.

Cross-linking between polypeptide chains of gelatin molecules in the gelatin capsule shell appearing after the capsules manufacture, i.e. during the storage, which results in formation of such (net-like) molecular gelatin structure in a shell which has reduced solubility in water.

Gelatin cross-linking in a gelatin capsule shell is induced by the incorporation of certain chemical agents in the fill or under stress conditions. Formation of a net-like molecular gelatin structure, which is almost insoluble or hardly soluble in water, results in impaired disintegration of the capsules with slower release of the active pharmaceutical ingredients contained in the capsules, resulting in impaired rupture test and dissolution test results.

The materials inducing the cross-linking in a capsule shell include any such material which: (a) supports cross-linking (formation of a cross bond) between polypeptides of gelatin molecules in gelatin capsule shell, or (b) slows down dissolution of capsules either with time and/or after their exposure to increased temperature or humidity. Preferred cross-linking induction agents include agents with carbonyl groups such as ketones, aldehydes and their derivatives. Agents inducing cross-linking in a gelatin shell usually contains a carbonyl group or its derivative or components which decomposes into carbonyl-containing decomposition products or their derivatives. Aldehyde moieties are preferred carbonyl-containing agent. Additionally, agents supporting or inducing cross-linking of gelatin molecules in gelatin capsule shell may contain aldehyde groups or components where decomposition results in the formation of aldehydes, especially formaldehyde.

The determination of whether the material in a capsule fill causes cross-linking in a capsule shell is matter of routine. For example, a capsule fill which contains material supporting cross-linking results in pellicle formation and produces slow dissolution, slow disintegration or slow rupture time of the capsule during the rupture test (according to USP 24, (26)), is observed, when the capsules are tested during accelerated stability study, i.e. in storage at 75% relative humidity and 40° C. for four weeks and more. The term "slow dissolution" or "impaired dissolution" means that the average 60-minute dissolution is reduced by at least 20% after the capsules are exposed to the conditions of the accelerated stability study. The term "delayed disintegration" means that the average disintegration time, as measured in disintegration test according to European Pharmacopoeia (27), is prolonged by at least 20% after the capsules are exposed to the above mentioned conditions of the accelerated stability study. The term "decelerated time of capsule rupture" means that average time of rupture, as measured in so-called dissolution test according to USP 24 in USP dissolution equipment No. 2 (26) is prolonged by at least 20% after the capsules are exposed to the above mentioned conditions of the accelerated stability study.

The presence of formaldehyde in the capsules after storage under conditions of the accelerated stability study has been found to support cross-linking in the shell of gelatin capsules. As it will be seen hereinafter (see FIG. 1), formaldehyde is thus useful to test the efficacy of the moieties and methods taught herein as it promotes cross-linking.

Another indicator of cross-linking influence is the optical observation of a pellicle, which is the insoluble residue of the gelatin shell, seen either in the disintegration, rupture or dissolution tests as shown in several examples hereinafter.

An "reducing effective amount" of a compound/moiety for reducing cross-linking is such an amount which is effective to improve the "dissolution after 60 minutes" parameter as denoted by a change of more than +/−20% of the starting value for gel capsules stored for 4 weeks under conditions of accelerated stability study and/or 9 months under room temperature conditions. In some embodiments, the change in dissolution observed for formulations according to the invention does not change by more than +/−10% of the original value. It is noted that the term "reducing" means preventing (entirely or in part) the onset of cross-linking, as well as reversing (entirely or in part) already existing cross-linking.

Another indicator that the amount of compound/moiety for reducing cross-linking is effective in the appearance of non-dissolved residues of gelatin in the solutions in disintegration, rupture or dissolution tests. The appearance of gelatin residues in solutions used in these tests should be the same after 4 weeks as compared to the beginning of the stability study for the capsules stored under conditions of accelerated stability. The agent inducing the cross-linking is preferably either the active pharmaceutical ingredient of the formulation itself and/or a pharmaceutical excipient or their combination. The agent inducing cross-linking can be, under certain conditions, an agent which is not described in the product composition itself but comes into direct contact with the product. Such agent can be, for example, a lubricant used in the manufacture of soft gelatin capsules or agents for reducing the static charge in the case of hard gelatin capsules.

Any active pharmaceutical agent which is suitable for administration in a form of gelatin capsules can also be used in gelatin capsules stabilized by the described method. However, the method described is especially advantageous for stabilization of such capsules which contain pharmacologically effective amount of such active pharmaceutical ingredients which, in the mixture with pharmaceutical excipients, create fills of the second group character described above. Such fills contain the water miscible liquids, e.g., polyethyleneglycols and non-iogenic surface active ingredients (surfactants) or lower alcohols. The water miscible agents are characterized by their capability to migrate into the gelatin shell of a capsule and the fills containing the water miscible agents are characterized by their capability, unlike the fills solely composed of lipophilic, water immiscible agents, to retain a certain part of the water penetrating into a capsule fill following encapsulation. In these fills, the process of reverse water resorption from the fill into the shell during capsules drying is more complex and a determination of the balance is conditioned by HI.B—value of fill and resorption hysteresis curves of gelatin shell of concrete composition (York, J. Pharm. Pharmacol. 33:269 (1981)).

These fills are known as self emulsions (SEDDS, Self Emulsifying Drug Delivery Systems), or self microemulsions (SMEDDS, Self MicroEmulsifying Drug Delivery Systems). See Barthélémy, et al., Liquid and Semi-solid Excipients in Hard Capsules, and Viscous SMEDDS Solutions. (Lecture given at Chatenay Malabry—Paris XI, Faculty of Pharmacy, during the Conference organized by APGI, Capsugel and Gattefossé on November 1994), Gattefossé company application list, PF95249—1$^{st}$ Edition April 95). Self emulsions are liquid or semi-solid isotropic mixtures of oleic phase and non-ionogenic tenzides or solvents and co-solvents having such character that they create the type of O/W (oil in water) emulsion in body fluids. Self microemulsions are water-free liquids or solid systems composed of oleic phase and non-ionogenic tensides or solvent and co-solvent having such character that they spontaneously create microemulsion in water or body fluids.

Pharmaceutical formulations of the above mentioned character are used for such active pharmaceutical ingredients as cyclic undecapeptides and taxanes or their combinations or combinations of these agents with inhibitors of cytochrome P450, such as e.g., macrolide antibiotics, calcium channel blockators, glucocorticoids, ergot alkaloids, and imidazolic and triazolic antimycotics. Or, such active pharmacological ingredients may include combinations of the first named group with inducers of cytochrome P450, such as anticonvulsives, sulfonamides and rifampicin or their combinations. The above mentioned list also contemplates all salts of the active pharmaceutical ingredients and is not limited with respect to the claims of the patent.

Pharmaceutically acceptable excipients are well known in the art. The term "acceptable" includes such agents which are described in the Handbook of Pharmaceutical Excipients published by American Pharmaceutical Association, Washington D.C., and/or in Inactive Ingredient Guide published by Food and Drug Administration (FDA). Especially useful pharmaceutically acceptable ingredients include monosaccharides such as e.g., glucose and fructose, disaccharides such as e.g., lactose and saccharose, trisaccharides, such as e.g., raffinose and polysaccharides such as e.g., starches (corn and potato starch), starch derivatives (pre-gelatinized starch), pectin and carrageenans, tenzides, especially non-ionogenic tenzides such as ethoxylated sorbitan (polysorbate Tween 80), lubricants such as e.g., magnesium stearate, stearyl sodium fumarate, hydrogenated vegetable oil, paraffin oil, fractionated corn oil, fractionated coconut oil, disintegration agents such as e.g., cross-linked povidon, binding agents such as e.g., povidon and pharmaceutically acceptable dyes and pigments such as e.g., FD&C red color No. 3.

In an embodiment, the agent inducing gelatin cross-linking in the gelatin shell is the pharmaceutical active ingredient and/or pharmaceutical excipient and/or their combination.

In some embodiments, the gelatin composition of the shell of the capsule contains from 0.1 to 10% of an amino-acid moiety, referred to dry matter. At the same time, the gelatin composition of the shell or capsule fill or lubricant oil used in the manufacture and/or combinations of these parts of gelatin capsule further contain from 0.01 to 10% of weight of an ester of carboxylic acid, referred to dry matter of the shell, i.e. weight of capsule fill.

Preferably, the gelatin composition of the shell of gelatin capsule contains from 0.2 to 5% of amino-acid moiety, referred to dry matter. At the same time, the gelatin composition of the shell or capsule fill or lubricant oil used in the manufacture and/or combinations of these parts of gelatin capsule further contains from 0.01 to 10 by weight of ester of carboxyl acid, referred to dry matter of the shell, or weight of capsule fill, respectively.

Without wishing to be bound to any specific mechanism, the inventors believe that the amino-acid component according to the invention, acts as a remover of free carbonyl groups, especially as a remover of formaldehyde, although the ability of amino-acids to act as acid and base may also be involved. The esters of carboxylic acid are expected to enable complete dissolution of amino-acid at the phase boundary of the gelatin gel of the shell and the liquid of inner capsule fill, which is critical for formation of pellicle.

Especially contemplated are amino-acids which contain both free carboxyl and amino groups, especially a primary amino-group, or its salt, namely both monomer amino-acids and short peptide chains composed of two or three amino-acid residues. Especially suitable are monomer amino-acids such as e.g., alpha and omega amino-acids. The most suitable are amino-acids of the group including acetylcysteine, glycine, tryptophan, lysine, leucine, threonine, aspartic acid, glutamic acid, asparagin, glutamine, arginine, cysteine, phenylalanine, tyrosine, histidine, valine, alanine, isoleucine, ornithine, p-aminobenzoic acid and nicotinic acid, or their salts. An especially suitable amino-acid is glycine.

In some embodiments an ester of carboxyl acid is used. The esters of carboxyl acids suitable for the described method are the residues of $C_4$-$C_{20}$ carboxyl acids containing one, two or three carboxyl (—COOH) groups or their salts esterically bound to one-, two- and polysaturated aliphatic or heterocyclic alcohols, branched and unbranched, with the chain length $C_3$-$C_{18}$, with the exception of esters of higher fatty acids and glycerol which are commonly used in a capsule fill as carrier.

The monomer residue of carboxyl acid moieties useful according to the invention may be a residue with 4-10 carbon atoms ($C_4$-$C_{10}$) or its salt and this carboxyl acid originally contained 1-3 carboxyl (—COOH) groups, preferably 2 carboxyl groups and came from the group of such agents such as benzoic acid, fumaric acid, malic acid, maleic acid, acetic acid, citric acid, ascorbic acid, ethylenediamintetraacetic acid, lactic acid, sorbic acid, tartaric acid, adipic acid, succinic acid and gluconic acid. Especially suitable are the residues of succinic, fumaric, acetic, citric, malic and tartaric acid. Esters of carboxyl acids or their salts are soluble in the composition of a gelatin capsule fill (if used as a component of the fill composition) or water (if used as a component of the shell composition) or lubricant (if used as a part of lubricant). Salts of the relevant carboxyl acids include the salts of alkaline metals, metals of alkaline soil and ammonia.

The application set forth especially relates to gelatin capsules whose fill has the character of self emulsions and contains water miscible liquids such as e.g., polyethyleneglycols and non-ionogenic surface active agents (surfactants) or lower alcohols. The water miscible agents are characterized by their ability to migrate into the gelatin gel of capsules and the fills containing the water miscible agents are characterized by their ability, unlike the fills solely composed of lipophilic, water non-miscible agents, to contain or retain a certain part of the water penetrating into a capsule fill after its encapsulation.

Another aspect of the invention relates to soft gelatin capsules as described above in which the fill contains an active pharmaceutical ingredient. The pharmacologically active amount of the compound may be chosen from among cyclic undecapeptides and taxanes or pharmacologically active amounts of their combinations and/or combinations of these agents with inhibitors of cytochrome P450 such as e.g., macrolidic antibiotics, calcium channel blockatots, glucocorticoids, ergot alkaloids and imidazolic and triazolic antimycotics, or such pharmacologically active agents can be the combinations of the first named group with inductors of cytochrome P450 such as anticonvulsives, sulfonamides and rifampicin or their combinations while the above mentioned list also relates to all salts of the pharmaceutically active agents. The described list is illustrative only and is not intended to limit the claims of the invention.

Furthermore, the invention especially relates to capsules whose fill contains tocopherol acetate and/or tocopherol succinate and/or d-alpha tocopheryl polyethylene glycol succinate (TPGS) as the ester of carboxyl group and whose gelatin shell contains glycine as amino-acid.

According to another aspect, the invention contemplates gelatin capsules which are stabilized by the described method.

The invention relates to gelatin capsules prepared by the above described method in which the agent inducing cross-linking in the gelatin of the gelatin shell is an active pharmaceutical ingredient or pharmaceutical excipient or their combinations; preferably to such capsules whose fill has the character of self emulsion and contains water miscible liquids such as e.g., polyethyleneglycols and non-ionogenic surface active agents (surfactants), or lower alcohols. Furthermore, it relates to such capsules in which pharmaceutical excipient is a pharmaceutically acceptable mixture of mono-, di- and triglycerides, pharmaceutically acceptable mixtures of esters of fatty acids and polyglycerols (n=1-10), pharmaceutically acceptable monosaccharide, disaccharide, oligosaccharide, polysaccharide or their mixture and/or tenzides such as e.g., mixtures of polyethoxylated vegetable or animal oils, polyethyleneglycols and lecithins.

The gelatin shell of gelatin capsules according to the invention contain an amino-acid moiety. Hence, capsules according to the invention contain an amino-acid moiety in the gelatin shell of the capsule and a suitable ester of carboxylic acid into the fill of the capsule and/or into the gelatin shell of the capsule and/or into the lubrication agent used during manufacturing process of the capsules, or into all of these three components at the same time. Preferably, the gelatin shell of the capsules contains 0.1-10% of weight of amino acid moiety and gelatin shell or capsule fill or lubricant used in the manufacture of capsules contains 0.01-10% by weight of an ester of carboxyl acid or its salt.

In some embodiments, the gelatin shell of the capsules contains 0.4-5% by weight of amino-acid and the gelatin shell or capsule fill or lubricant used in the manufacture of capsules contains 0.01-10% by weight of an ester of carboxyl acid or its salt.

The advantage of gelatin capsules prepared according to the disclosed method is that the rupture time (measured in the rupture test by means of dissolution apparatus of type II according to USP 24 (e.g., according to USP article for cyclosporin-containing gelatin capsules)), dissolution test for gelatin capsules (USP 24, method <711>, page 1941) and/or the result of disintegration test (according to PhEur3) remains stable during the accelerated stability study. The submitted invention further relates to the capsules described above in which the rupture time in the rupture test remains in a range +/−20%, preferably +/−0% after 4-weeks of storage at temperature of 40+/−2° C. and 75% relative humidity with respect to the original rupture time value before the start of the stability study; and/or that the dissolution test carried out according to USP 24 method <711>, page 1941 for 60 minutes remains in a range +/−20%, preferably +/−10% after 4-weeks of storage at temperature of 40+/−2° C. and 75% relative humidity with respect to the original dissolution value before the start of stability tests; and/or that the disintegration time measured in disintegration test of capsules according to PhEur 3 remains in a range +/−20%, preferably +/−10% after 4-week storage at temperature 40+/−2° C. and 75% relative humidity, with respect to the original dissolution value before the start of stability testing. At the same time it is expected that the initial values of parameters and parameters after the end of the stability test are measured by the same gauge or determined by the same method.

The details of one or more embodiments of the invention are set forth in the accompanying description above. Although any methods and materials similar or equivalent to those described herein can be used in the practice or testing of the present invention, the preferred methods and materials are now described. Other features, objects, and advantages of the invention will be apparent from the description and from the claims. In the specification and the appended claims, the singular forms include plural referents unless the context clearly dictates otherwise. Unless defined otherwise, all technical and scientific terms used herein have the same meaning as commonly understood by one of ordinary skill in the art to which this invention belongs. All patents and publications cited in this specification are incorporated by reference.

EXAMPLES

The following EXAMPLES are presented in order to more fully illustrate the preferred embodiments of the invention. These EXAMPLES should in no way be construed as limiting the scope of the invention, as defined by the appended claims.

Example 1

Rupture Test of Cyclosporine Capsules with Formaldehyde Addition

To illustrate the efficacy of representative embodiments of the invention capsules prepared as described herein (see specifics described in Table 1) were treated with formaldehyde (known to promote cross-linking) and scored over time. For this purpose, 36.5% formaldehyde solution was injected into the fill of the capsules to reach 0.3% final concentration in the capsule fill (capsules 5 oval—2 μl, 20 oblong capsules—8.5 μl of 36.5% formaldehyde solution). The pinhole created by the injection needle was covered with melted gelatin solution of the same composition as capsule itself. After injection, individual capsules were placed into a thermobox under 40° C. for 15-16 hours to promote cross-linking. After the treatment was completed, capsules were placed into a conventional dissolution apparatus and under standard dissolution test conditions. Shell rupture time, fill release time, and the appearance of a pellicle after 60 min were evaluated. Results are given in the Table 1, where the code of treatment shows the reference to capsule fill and shell compositions as well as the capsule size. Experimental variants with code "0" for the type of gel composition were prepared according to Table B below. Experimental variants with code "G" for the type of gel composition were prepared according to Table F below. Experimental variants with code "0" for the type of cross-linking inhibition enhancer were prepared according to Table A below. Experimental variants with code "T" for the type of cross-linking inhibition enhancer were prepared according to Table C below.

When comparing fill release time with shell rupture time, it can be seen that in all samples but the last one (row 6 containing both cross-linking inhibitor and cross-linking inhibition enhancer) the fill release time is substantially longer than the shell rupture time. Only in samples with glycine (row 5 and 6), no pellicle was observed after 60 min in dissolution media.

TABLE 1

Comparison of Shell rupture time, Fill release time and Pellicle appearance of soft gelatin capsules with various degrees or resistance against cross-linking

| Dissolution conditions: | Dissolution medium: | | | | | | | | | | | | | | |
|---|---|---|---|---|---|---|---|---|---|---|---|---|---|---|---|
| Temperature 37° C. Rotations 75 rpm | For capsules 5 oval 500 ml dissolution liquid volume N,N-dimethyldo-decylamine-N-oxide 2 g/110.1M HCl | | | | | | | For capsules 20 oblong 1000 ml dissolution liquid volume N,N-dimethyldo-decylamine-N-oxide 4 g/110.1M HCl | | | | | | | |

| | | Code of | Shell rupture time [min] | | | | | | | Fill release time [min] | | | | | |
|---|---|---|---|---|---|---|---|---|---|---|---|---|---|---|---|
| | Batch No. | treatment | 1 | 2 | 3 | 4 | 5 | 6 | Ø | 1 | 2 | 3 | 4 | 5 | 6 | Ø |
| 1 | 4T104004/A | 00100 | 5 | 4 | 4 | 4 | 4 | 10 | 5.2 | 9 | 9 | 9 | 12 | 12 | 12 | 10.5 |
| 2 | 4T104004/B | 0T100 | 4 | 4 | 2 | 6 | 6 | 6 | 4.7 | 7.5 | 9.5 | 9 | 9 | 9 | 9 | 8.8 |
| 3 | 4T104005/A | 0025 | 13 | 10 | 10 | 15 | 6 | 10 | 10.7 | 22 | 19 | 17 | 18 | 20 | 19 | 19.2 |
| 4 | 4T104005/B | 0T25 | 7.5 | 6 | 7.5 | 14 | 7.5 | 13 | 9.3 | 15 | 16.5 | 18 | 17 | 15.5 | 16 | 16.3 |
| 5 | 4T104006/A | G0100 | 4 | 2 | 6 | 6 | 6 | 4 | 4.7 | 7 | 7.5 | 7.5 | 8 | 7.5 | 7 | 7.4 |
| 6 | 4T104006/B | GT100 | 5 | 9 | 7 | 5 | 7 | 8 | 6.3 | 7 | 6.5 | 9 | 7 | 5 | 8 | 6.8 |

Pellicle appearance after 60 min

1. Vessels No. 1, 4 - cca 0.5-1 mm pellicle; Vessels No. 2, 3, 5, 6 - capsule is divided into two scissors-like ("V"-like) parts, pellicle has the size of capsule
2. Vessels No. 1, 2, 3, 5, 6 - pellicle is <1 mm, Vessel No. 4 - pellicle cca 1 mm
3. Vessels No. 1, 2, 3, 4, 5, 6 - after cca 17 min capsules divided in seam into two "V" - like parts, whose appearance did not change as long as 60 min
4. Vessels No. 2 - gelatin residuum flowing in the medium, Vessels No. 1, 3, 4, 5, 6 - after cca 20 min capsules divided in seam into two "V" - like parts, whose appearance did not change as long as 60 min TABLE 1-continued Comparison of Shell rupture time, Fill release time and Pellicle appearance of soft gelatin capsules with various degrees or resistance against cross-linking 5  Vessels No. 2 - 1 mm gelatin residual at the bottom of the vessel
Vessels No. 1, 3, 4, 5, 6 - capsule is dissolved completely
6  Vessels No. 1, 2, 3, 4, 6 - less than 0.5 mm gelatin residual at the bottom of the vessel
Vessels No. 5 - capsule is dissolved completely Legend for code of treatment:
Type of gel composition: G - with glycine
Type of enhancer in the fill: 0 - no enhancer, T - tocopherol
Capsule size: 100 - cps 20 oblong, 25 - cps 5 oval

Example 2

Cross-Linking Promoted by Placebo Components and Under Accelerated Stability Conditions

Placebo without Ester of Carboxylic Acid

A pharmaceutical composition according to the Table A was encapsulated into a soft gelatin capsule. The gelatin composition was as described in Table B and thus did not contain glycine and neither the gel, nor the fill and nor the lubricant contained ester of carboxylic acid. Results are given in the Tables 2-4. After 8 weeks under standard accelerated stability conditions (Table 4), a pellicle was observed (rupture test).

TABLE A

Pharmaceutical composition for soft gelatin capsule fill without cross-linking inhibition enhancer

| Material | Int. Code | Content (% w/w) | Weight per batch (kg) |
|---|---|---|---|
| Dehydrated ethanol | 38 021 00 | 14.7 | 9.261 |
| Polyoxl-40-hydrogenated castor oil | 37 874 02 | 30.4 | 19.165 |
| Polyglyceryl-10-oleate | 37 873 02 | 20.6 | 13.003 |
| Polyglyceryl-3-oleate | 37 872 02 | 34.4 | 21.685 |
| Total | | 100 | 63.114 |

TABLE B

Gel composition for soft gelatin capsule shell without cross-linking inhibitor (without glycine)

| Material | Code | Content (% w/w) | Weight per batch (kg) |
|---|---|---|---|
| Gelatin | 3802200 | 44.0 | 110 |
| Glycerol 85% | 1481104 | 20.0 | 50.0 |
| Sorbitol sol 70% | 3625402 | 4.0 | 10.0 |
| Purified water, USP 24 | 3822800 | 32.0 | 80.0 |
| Total | | 100.0 | 250.0 |

TABLE 2

SOFT GELATIN CAPSULES WITH PLACEBO, STARTING ANALYSIS T = 0

| Batch No./Code of treatment | | cross-linking inhibitor | Ethanol [%] | Peroxide value | Aldehydes mg/kg | Water in fill [%] | Shell rupture time [min] | Fill release time [min] | Gelatin residuum after 60 min | Pellicle appearance after 60 min |
|---|---|---|---|---|---|---|---|---|---|---|
| 4T104004/A | 00100 | NO (without glycine) | 11.0 | 0.72 | 44.85 | 2.25 | 3:00 | 3:00 | 1 mm | not present |
| 4T104004/B | OT100 | | 10.9 | 0.90 | 49.73 | 2.18 | 2:55 | 2:55 | 2.5 mm | not present |
| 4T104004/C | OA100 | | 12.7 | 0.31 | 43.73 | 2.07 | 1:20 | 1:45 | 4 mm | not present |
| 4T104004/D | OAT100 | | 11.4 | 0.31 | 48.05 | 2.03 | 1:25 | 1:40 | 5 mm | not present |
| 4T104005/A | 0025 | | 10.5 | 0.81 | 49.39 | 2.04 | 2:20 | 4:00 | 1 mm | not present |
| 4T104005/B | OT25 | | 10.8 | 1.09 | 49.25 | 2.02 | 4:00 | 4:00 | <1 mm | not present |
| 4T104006/A | G0100 | YES (with glycine) | 10.9 | 0.78 | 48.70 | 2.14 | 2:00 | 2:00 | <1 mm | not present |
| 4T104006/B | GT100 | | 10.9 | 0.86 | 41.63 | 2.27 | 1:30 | 1:30 | 4 mm | not present |
| 4T104006/C | GA100 | | 12.1 | 0.27 | 40.99 | 2.17 | 2:20 | 5:00 | 3 mm | not present |
| 4T104006/D | GAT100 | | 12.3 | 0.45 | 45.22 | 2.08 | 2:00 | 2:00 | 3 mm | not present |
| 4T104006/E | GT100EL | | 11.3 | 0.90 | 46.15 | 2.17 | 2:30 | 2:50 | 0.5 mm | not present |
| 4T104004/A + PS | G0100PS | | 11.0 | 0.58 | 44.46 | 1.59 | 5:20 | 7:00 | 1 mm | not present |

Legend for code of treatment:
Type of gel composition: G - with glycine
Type of enhancer in the fill: 0 - no enhancer, T - tocopherol acetate, A - ascorbyl palmitate
Capsule size: 100 - cps 20 oblong, 25 - cps 5 oval
PS - prolonged drying
EL - capsules washed in Ethanol batch containing Lecitin

TABLE 3

SOFT GELATIN CAPSULES WITH PLACEBO, ANALYSIS AT T = 2 WEEKS

| Batch No./Code of treatment | | cross-linking inhibitor | Ethanol [%] | Peroxide value | Aldehydes g/kg | Water in fill [%] | Shell rupture time [min] | Fill release time [min] | Gelatin residuum after 60 min | Pellicle appearance after 60 min |
|---|---|---|---|---|---|---|---|---|---|---|
| 4T104004/A | 00100 | NO (without glycine) | na | 0.53 | 62.12 | 2.15 | 7:10 | 8:10 | 4 mm | not present |
| 4T104004/B | OT100 | | na | 0.87 | 63.91 | 2.14 | 16.10 | 17:45 | 2 mm | not present |
| 4T104004/C | OA100 | | na | 0.23 | 56.63 | 2.08 | 1:55 | 7:00 | 5 mm | present, cca 1 cm |
| 4T104004/D | OAT100 | | na | 0.29 | 49.58 | 2.01 | 1:20 | 9:00 | 6 mm | present |
| 4T104005/A | 0025 | | na | 0.59 | 58.50 | 1.97 | 4:30 | 6:10 | 2 mm | not present |
| 4T104005/B | OT25 | | na | 1.00 | 60.98 | 1.96 | 5:19 | 7:10 | 5 mm | not present |
| 4T104006/A | G0100 | YES (with glycine) | na | 0.61 | 51.64 | 2.11 | 3:20 | 6:30 | 1 mm | not present |
| 4T104006/B | GT100 | | na | 0.67 | 60.33 | 2.26 | 6:00 | 7:00 | 2 mm | not present |
| 4T104006/C | GA100 | | na | 0.19 | 53.34 | 2.14 | 2:20 | 7:00 | 4 mm | not present |
| 4T104006/D | GAT100 | | na | 0.23 | 52.93 | 2.06 | 1:30 | 6:10 | — | not present |
| 4T104006/E | GT100EL | | na | 0.70 | 58.28 | 2.13 | 2:00 | 7:00 | 3 mm | not present |
| 4T104004/A + PS | G0100PS | | na | 0.59 | 43.54 | 1.55 | 11:35 | 12:00 | 2 mm | not present |

Legend for code of treatment:
Type of gel composition: G - with glycine
Type of enhancer in the fill: 0 - no enhancer, T - tocopherol acetate, A - ascorbyl palmitate
Capsule size: 100 - cps 20 oblong, 25 - cps 5 oval
PS - prolonged drying
EL - capsules washed in Ethanol batch containing Lecitin

TABLE 4

SOFT GELATIN CAPSULES WITH PLACEBO, ANALYSIS AT T = 4 WEEKS

| Batch No./Code of treatment | | cross-linking inhibitor | Ethanol [%] | Peroxide value | Aldehydes g/kg | Water in fill [%] | Shell rupture time [min] | Fill release time [min] | Gelatin residuum after 60 min | Pellicle appearance after 60 min |
|---|---|---|---|---|---|---|---|---|---|---|
| 4T104004/;A | 00100 | NO (without glycine) | na | 0.72 | 40.51 | 2.16 | 6:00 | 12:00 | 4 mm | present |
| 4T104004/B | OT100 | | na | 1.42 | 46.83 | 2.16 | 7:00 | 10:00 | 5 mm | present |
| 4T104004/C | OA100 | | na | 0.22 | 42.67 | 2.06 | 9:00 | 12:00 | 5 mm | present |
| 4T104004/D | OAT100 | | na | 0.37 | 40.94 | 1.99 | 7:00 | 23:00 | 10 mm | present |
| 4T104005/A | 0025 | | na | 0.85 | 44.45 | 2.01 | 7:00 | 10:00 | 6 mm | present |
| 4T104005/B | OT25 | | na | 1.81 | 47.74 | 2.00 | 6:00 | 10:00 | 6 mm | present |
| 4T104006/A | G0100 | YES (with glycine) | na | 0.65 | 38.92 | 2.12 | 3:00 | 7:00 | 2 mm | present |
| 4T104006/B | GT100 | | na | 1.17 | 40.15 | 2.24 | 6:00 | 8:00 | <1 mm | present |
| 4T104006/C | GA100 | | na | 0.28 | 33.20 | 2.12 | 4:00 | 7:00 | 4 mm | present |
| 4T104006/D | GAT100 | | na | 0.29 | 27.78 | 2.08 | 3:00 | 5:00 | 1 mm | present |
| 4T104006/E | GT100EL | | na | 1.01 | 39.34 | 2.16 | 3:00 | 7:00 | 3 mm | present |
| 4T104004/A + PS | G0100PS | | na | 0.74 | 40.49 | 1.51 | 4:00 | 5:00 | 3 mm | present |

Legend for code of treatment:
Type of gel composition: G - with glycine
Type of enhancer in the fill: 0 - no enhancer, T - tocopherol acetate, A - ascorbyl palmitate
Capsule size: 100 - cps 20 oblong, 25 - cps 5 oval
PS - prolonged drying
EL - capsules washed in Ethanol batch containing Lecitin

Example 3

Cross-Linking Promoted by Placebo Components and Under Accelerated Stability Conditions

Placebo with Cross-Linking Inhibition Enhancer Only

A pharmaceutical composition according to the Table C was encapsulated into a soft gelatin capsule, where the gelatin composition according to the Table B (supra) did not contain cross-linking inhibitor and neither the gel, nor the lubricant contained cross-linking inhibition enhancer (ester of carboxylic acid, tocopherol acetate), but the fill did.

Results are given in the Tables 2-4 (supra). After 8 weeks in accelerated stability conditions (Table 4), a pellicle was observed (rupture test).

TABLE C

Pharmaceutical composition for soft gelatin capsule fill with cross-linking inhibition enhancer - tocopherol

| Material | Code | Content (% w/w) | Weight per batch (kg) |
|---|---|---|---|
| Dehydrated ethanol | 38 021 00 | 14.7 | 9.261 |
| Polyoxyl-40-hydrogenated castor oil | 37 874 02 | 30.3 | 19.165 |
| Polyglyceryl-10-oleate | 37 873 02 | 20.6 | 13.003 |
| Polyglyceryl-3-oleate | 37 872 02 | 34.3 | 21.685 |
| Tocopherol acetate | 36 594 00 | 0.2 | 0.126 |
| Total | | 100 | 63.24 |

Example 4

Cross-Linking Promoted by Placebo Components and Under Accelerated Stability Conditions Placebo with Ester of Carboxylic Acid-Ascorbyl Palmitate A pharmaceutical composition according to the Table D was encapsulated into a soft gelatin capsule, where the gelatin composition did not contain glycine and neither the gel, nor the lubricant contained ester of carboxylic acid, but the fill did.

Results are given in the Tables 2-4 (supra). After 8 weeks in accelerated stability conditions (Table 4 (supra)), pellicle was observed (rupture test).

TABLE D

Pharmaceutical composition for soft gelatin capsule fill with cross-linking inhibition enhancer - with ascorbyl palmitate

| Material | Code | Content (% w/w) | Weight per batch (kg) |
| --- | --- | --- | --- |
| Dehydrated ethanol | 38 021 00 | 14.7 | 0.735 |
| Polyoxyl-40-hydrogenated castor oil | 37 874 02 | 30.3 | 1.515 |
| Polyglyceryl-10-oleate | 37 873 02 | 20.6 | 1.03 |
| Polyglyceryl-3-oleate | 37 872 02 | 34.3 | 1.715 |
| Ascorbyl palmitate | 10 391 03 | 0.02 | 0.001 |
| Total | | 100 | 5.001 |

Example 5

Cross-Linking Promoted by Placebo Components and Under Accelerated Stability Conditions Placebo with Two Cross-Linking Inhibition Enhancers—Ascorbyl Palmitate and Tocopherol Acetate A placebo of a pharmaceutical composition according to Table E was encapsulated into a soft gelatin capsule, where the gelatin composition according to Table B did not contain glycine and neither the gel, nor the lubricant contained esters of carboxylic acid, but the fill did.

Results are given in the Tables 2-4 (supra). After 8 weeks in accelerated stability conditions (Table 4 (supra)), pellicle was observed (rupture test).

TABLE E

Pharmaceutical composition for soft gelatin capsule fill with cross-linking inhibition enhancers - with tocopherol acetate and ascorbyl palmitate

| Material | Code | Content (% w/w) | Weight per batch (kg) |
| --- | --- | --- | --- |
| Dehydrated ethanol | 38 021 00 | 14.7 | 0.735 |
| Polyoxyl-40-hydrogenated castor oil | 37 874 02 | 30.3 | 1.515 |
| Polyglyceryl-10-oleate | 37 873 02 | 20.6 | 1.03 |
| Polyglyceryl-3-oleate | 37 872 02 | 34.3 | 1.715 |
| Tocopherol acetate | 36 594 00 | 0.2 | 0.01 |
| Ascorbyl palmitate | 10 391 03 | 0.02 | 0.001 |
| Total | | 100 | 5.001 |

Example 6

Cross-Linking Promoted by Placebo Components and Under Accelerated Stability Conditions Placebo without Esters of Carboxylic Acid, Glycine in Gelatin A pharmaceutical composition according to Table A was encapsulated into a soft gelatin capsule, where the gelatin composition according to Table F did contain glycine, but neither the gel, nor the lubricant, nor the fill contained esters of carboxylic acid.

Results are given in the Tables 2-4 (supra). After 8 weeks in accelerated stability conditions (Table 4 (supra)), pellicle was observed (rupture test). However, the fill-release time was still under 10 min and the gelatin residuum after 60 min was smaller than in variants without glycine.

TABLE F

Gel composition for soft gelatin capsule shell with cross-linking inhibitor (with glycine)

| Material | Code | Content (% w/w) | Weight per batch (kg) |
| --- | --- | --- | --- |
| Gelatin | 3802200 | 43.8 | 110.0 |
| Glycine | 3802200 | 0.452 | 1.135 |
| Glycerol 85% | 1481104 | 19.9 | 50.0 |
| Sorbitol sol. 70% | 3625402 | 4.0 | 10.0 |
| Purified water, USP 24 | 3822800 | 31.9 | 80.0 |
| Total | | 100 | 251.135 |

Example 7

Cross-Linking Promoted by Placebo Components and Under Accelerated Stability Conditions Placebo with Ester of Carboxylic Acid, Tocopherol Acetate, and Glycine in Gelatin A pharmaceutical composition according to Table C was encapsulated into a soft gelatin capsule, where the gelatin composition according to Table F did contain glycine and the fill contained ester of carboxylic acid, tocopherol acetate.

Results are given in Tables 2-4 (supra). After 8 weeks in accelerated stability conditions (Table 4 (supra)), pellicle was observed (rupture test). However, the fill-release time was still under 10 min and the gelatin residuum after 60 min was less than 1 mm and smaller than in variants without ester of carboxylic acid.

Example 8

Cross-Linking Promoted by Placebo Components and Under Accelerated Stability Conditions Placebo with Ester of Carboxylic Acid, Glycine in Gelatin A pharmaceutical composition according to Table D was encapsulated into a soft gelatin capsule, where the gelatin composition according to Table F did contain glycine and the fill contained esters of carboxylic acid, ascorbyl palmitate.

Results are given in Tables 2-4 (supra). After 8 weeks in accelerated stability conditions (Table 4 (supra)), pellicle was observed (rupture test). However, the fill-release time was still under 10 min and the gelatin residuum after 60 min was smaller than in variant without glycine.

Example 9

Cross-Linking Promoted by Placebo Components and Under Accelerated Stability Conditions: Placebo with Esters of Carboxylic Acid, Glycine in Gelatin A pharmaceutical composition according to Table E was encapsulated into a soft gelatin capsule, where the gelatin composition according to Table F did contain glycine and the fill contained ester of carboxylic acid, tocopherol acetate and ascorbyl palmitate.

Results are given in Tables 2-4 (supra). After 8 weeks in accelerated stability conditions (Table 4 (supra)), pellicle was observed in rupture test. However, the fill release time was still under 10 min and the gelatin residuum after 60 min was as small as 1 mm and smaller than in variants without ester of carboxylic acid.

Example 10

Figure 1:
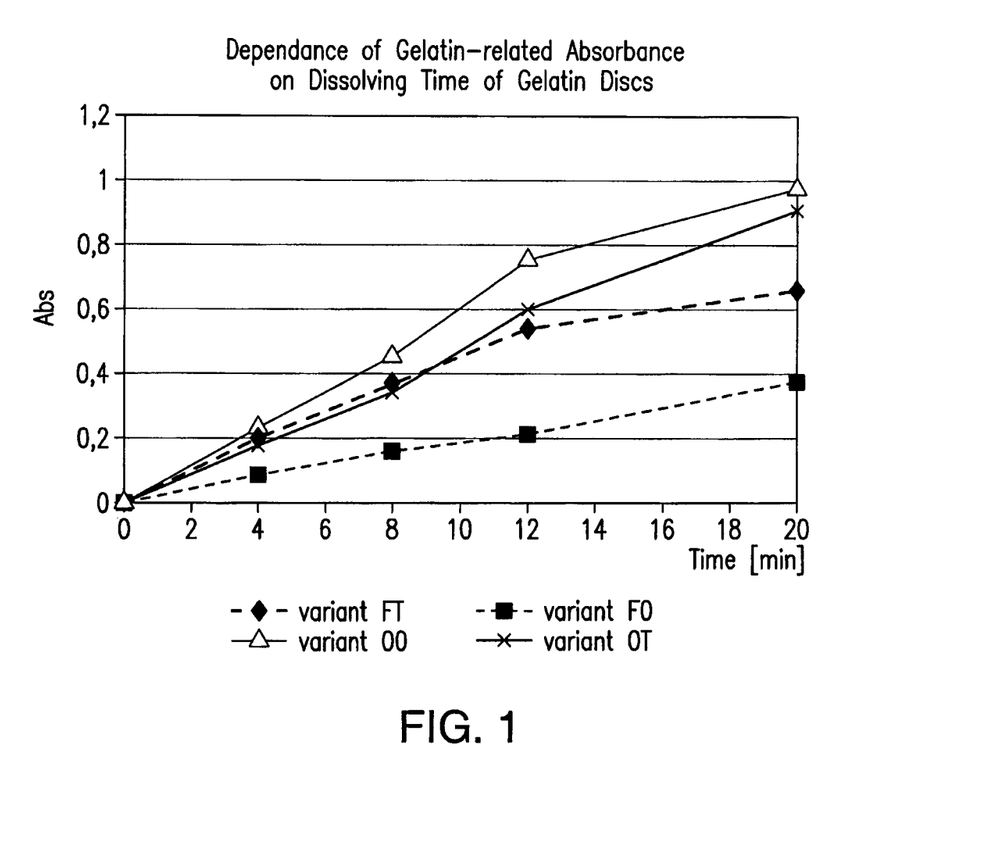
FIG. 1 is a graphical representation (absorbance over time) comparing the dissolution of representative formulations according to the invention. As described in more details hereinafter, FT is a glycine containing formulation containing formaldehyde and TPGS, FO is a glycine containing formulation containing formaldehyde and no TPGS, OO is a glycine containing formulation which does not contain formaldehyde or TPGS, OT is a glycine containing formulation which does not contain formaldehyde but does contain TPGS.

Cross-Linking Promoted by Placebo Components and Under Accelerated Stability Conditions Placebo with Another Ester of Carboxylic Acid—TPGS, Glycine in Gelatin A pharmaceutical composition was prepared in 4 samples according to Table G. On a lab scale, gelatin composition according to Table G containing glycine was prepared. Thin films were casted and round discs of gelatin ribbon were cut out from the films. Subsequently, 6 discs of the gelatin film were immersed into each one of the variant of the fill compositions listed in Table G. After 20 hours treatment at room temperature, discs were washed and placed into 50 ml of distilled water, thermostated at 37° C. and shaked to dissolve. Samples were taken after 4, 8, 12 and 20 min and content of free, dissolved gelatin in the solution was measured by direct spectrophotometry at 275 nm.

Dissolving curves in FIG. 1 show that variant with TPGS (FT, blue dashed curve) displays an improved dissolution characteristic after treatment with placebo solution containing aldehydes as compared to the sample without TPGS (FO, red variant).

TABLE G

Pharmaceutical composition for soft gelatin capsule fill in 4 variants with/without cross-linking inhibition enhancer and with/without cross-linking promoter

| | | Composition [% w/w] | | | |
|---|---|---|---|---|---|
| Material | Quality Standard | Valiant 00 | Variant F0 | Variant 0T | Variant FT |
| Dehydrated alcohol | SS/QC/3802100/00 | 14.70 | 14.70 | 14.70 | 14.70 |
| Polyoxyl-40-hydrogenated castor oil | SS/QC/3787403/00 | 30.43 | 30.43 | 30.43 | 30.43 |
| Polyglycerol-3-oleate | SS/QC/3787202/00 | 34.23 | 34.18 | 33.23 | 33.18 |
| Polyglycerol-10-oleate | SS/QC/3787302/00 | 20.64 | 20.64 | 20.64 | 20.64 |
| TPGS | Fluka Chemie GmbH | — | — | 1.0 | 1.0 |
| Formaldehyde solution 36.5% (w/w) | Fluka Chemie GmbH | — | 0.05 | — | 0.05 |
| Total | | 100.0 | 100.0 | 100.0 | 100.0 |

TABLE H

Gel composition for soft gelatin capsule shell with cross-linking inhibitor (with glycine)

| Material | Code | Content (% w/w) | Weight per batch (kg) |
|---|---|---|---|
| Gelatin | 3802200 | 45.0 | 450.0 |
| Glycin | 3802200 | 0.454 | 4.54 |
| Glycerol 85% | 1481104 | 20.0 | 200.0 |
| Sorbitol sol. 70% | 3625402 | 4.0 | 40.0 |
| Purified water, USP 24 | 3822800 | 30.546 | 305.5 |
| Total | | 100 | 1000.0 |

Example 11

Gelatin Capsules with Cyclosporine as the Active Ingredient in the Capsule Fill, with Cross-Linking Inhibition Enhancer in the Fill and Cross-Linking Inhibitor in the shell in Comparison to Gelatin Capsules with Cyclosporine as the Active Ingredient without with Cross-Linking Inhibition Enhancer in the Fill and without Cross-Linking Inhibitor in the Shell Cyclosporine was used in this experiment to exemplify the benefits of the instant invention for an active pharmaceutical ingredient/agent formulated in an ethanol-containing formulation encapsulated into a soft gelatin capsule.

In parallel samples Cyclosporine preparations were formulated with and without representative inhibitors and the inhibitor-enhancers according to the invention.

Figure 2A:
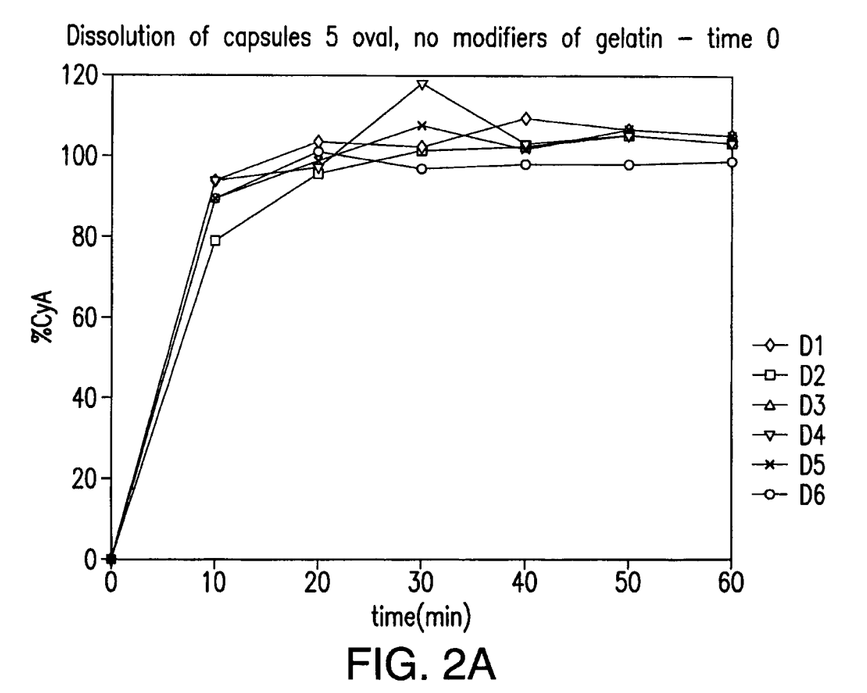
FIG. 2A is a graphical representation showing the dissolution of 6 samples (labeled D1-D6) with no modifier at time 0.
Figure 2B:
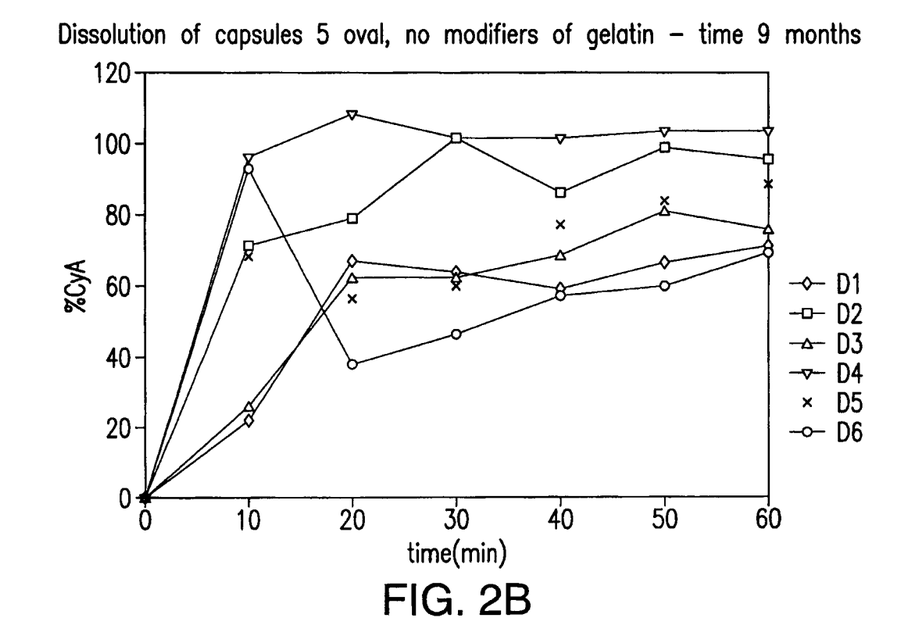
FIG. 2B is a graphical representation showing the dissolution of 6 samples (labeled D1-D6) with no modifier at time 9 months.
Figure 2C:
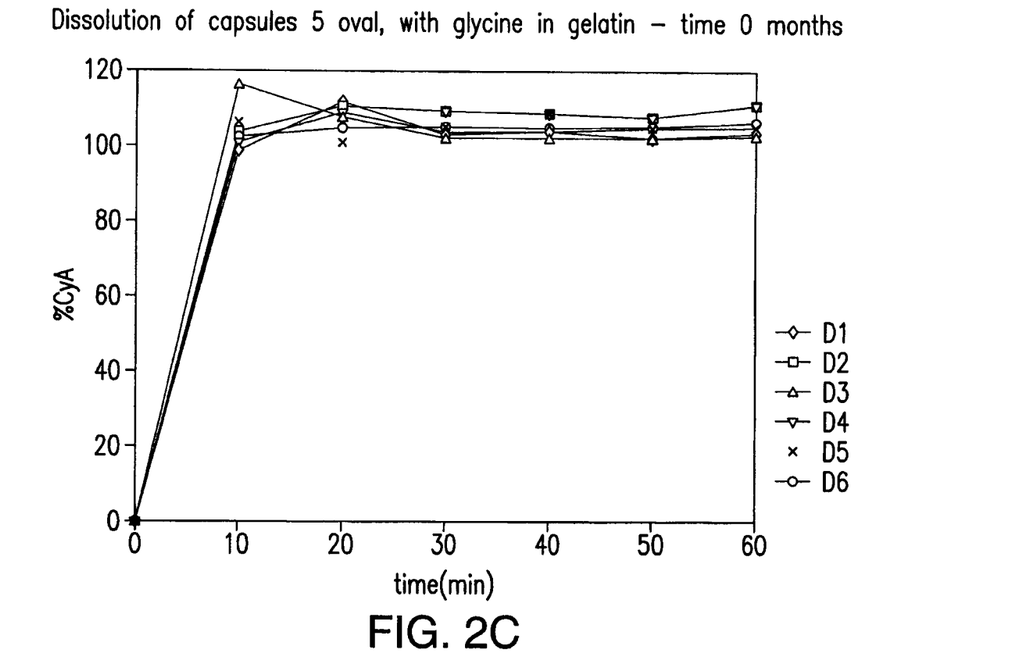
FIG. 2C is a graphical representation showing the dissolution of 6 samples (labeled D1-D6) with glycine at time 0.
Figure 2D:
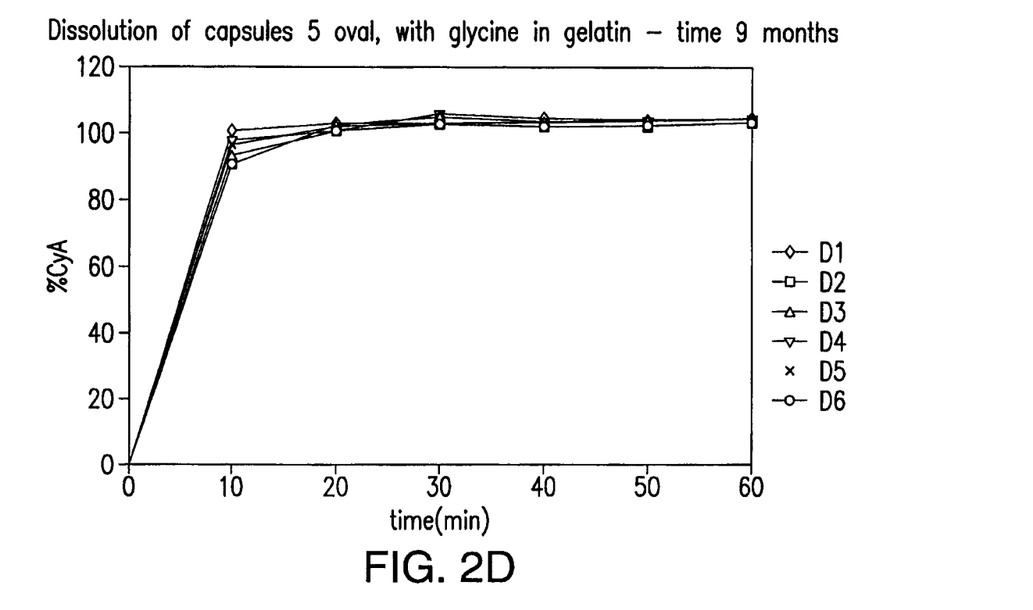
FIG. 2D is a graphical representation showing the dissolution of 6 samples (labeled D1-D6) with glycine at time 9 months.

(A) With Cross-Linking Inhibition Enhancer in the Fill and Cross-Linking Inhibitor in the Shell Accordingly, capsules (5 oval size) were prepared with a gelatin composition containing glycine, and the fill containing tocopherol acetate (see the composition of the fill in Table I and composition of the shell in Table J). After 8 weeks under standard accelerated stability conditions, pellicles were not observed (rupture test). After 9 months under controlled room temperature (CRT) conditions, pellicles were not observed (rupture test). After 9 months under CRT conditions, dissolution testing showed a pattern similar to that observed at time 0 (see FIG. 2d, and compare to FIG. 2c).

(B) Without Cross-Linking Inhibition Enhancer in the Fill and Cross-Linking Inhibitor in the Shell Cyclosporine was encapsulated into a soft gelatin capsule, where the gelatin composition did not contain glycine and the fill did not contain ester of carboxylic acid, tocopherol acetate (see the composition of the fill in Table K and composition of the shell in Table L).

After 8 weeks under accelerated stability conditions, pellicles were observed in some samples (rupture test). After 9 months under CRT conditions, pellicles were observed (rupture test). After 9 months, results of dissolution test were found to be non-satisfactory and much worsened when compared to that from starting conditions (see FIG. 2b and compare to FIG. 2a). More significantly, cross-linking inhibition as measured by dissolution profile testing can be observed when comparing the results for samples WITH the inhibitors and inhibitor-enhancers according to the invention as compared to samples WITHOUT (see FIG. 2b, and compare to FIG. 2d).

TABLE I

Pharmaceutical composition for soft gelatin capsule fill 5 oval with cross-linking inhibition enhancer (tocopherol acetate)

Quali-quantitative composition

| Material | Function | Composition [% w/w] | Composition [mg/capsule] |
|---|---|---|---|
| Cyclosporine | Active Ingredient | 9.21 | 25.0 |
| Dehydrated Alcohol | Solvent | 14.70 | 39.9 |
| Polyoxyl 40 Hydrogenated Castor Oil | Emulsifier | 27.14 | 73.7 |
| Polyglycerol (3) Oleate | Emulsifier | 30.45 | 82.7 |
| Polyglycerol (10) Oleate | Emulsifier | 18.41 | 50.0 |
| Tocopherol acetate | Cross-linking inhibition enhancer | 0.09 | 0.25 |
| Total | | 100.0 | 271.5 |

TABLE J

Gel composition for soft gelatin capsule shell with cross-linking inhibitor (with glycine)

| Material | Function | Content [% w/w] | Composition [mg/capsule] |
|---|---|---|---|
| Gelatin | Film Former; Gelling Agent | 63.5 | 95.3 |
| Purified water | Solvent | Added during preparation of Gelatin mass, with some removal during processing. Final filled capsules dried to moisture limit in shell of less than 15% | |
| Glycine | Prevents gelatin cross-linking; cross-linking inhibitor | 0.72 | 11 |
| Glycerol 85%, Sorbitol sol. 70% | Plasticizer; Diluent Plasticizer | 29.9 5.77 | 44.8 8.7 |
| Ferric Oxide, yellow | Colorant | 0.10 | 0.2 |
| Titanium Dioxide | Colorant | 0.72 | 1.1 |
| Total | | 100.71[1] | 151.2 mg |

[1]Calculated on the dried basis

TABLE K

Pharmaceutical composition for soft gelatin capsule fill without cross-linking inhibition enhancer (without tocopherol acetate)

Quali-quantitative composition

| Material | Function | Composition [% w/w] | Composition [mg/capsule] |
|---|---|---|---|
| Cyclosporine | Active Ingredient | 9.21 | 25.0 |
| Dehydrated Alcohol | Solvent | 14.70 | 39.9 |
| Polyoxyl 40 Hydrogenated Castor Oil | Emulsifier | 27.14 | 73.7 |
| Polyglycerol (3) Oleate | Emulsifier | 30.45 | 82.7 |
| Polyglycerol (10) Oleate | Emulsifier | 18.41 | 50.0 |
| Total | | 99.91 | 271.3 |

TABLE L

Gel composition for soft gelatin capsule shell without cross-linking inhibitor (without glycine)

| Material | Function | Content [% w/w] | Composition [mg/capsule] |
|---|---|---|---|
| Gelatin | Film Former; Gelling Agent | 63.5 | 95.3 |
| Purified water | Solvent | Added during preparation of Gelatin mass, with some removal during processing. Final filled capsules dried to moisture limit in shell of less than 15% | |
| Glycerol 85%, Sorbitol sol. 70% | Plasticizer; Diluent Plasticizer | 29.9 5.77 | 44.8 8.7 |
| Ferric Oxide, yellow | Colorant | 0.10 | 0.2 |
| Titanium Dioxide | Colorant | 0.72 | 11 |
| Total | | 99.99[1] | 151.2 mg |

[1]Calculated on the dried basis

While the claimed invention has been described in detail and with reference to specific embodiments thereof, it will be apparent to one of ordinary skill in the art that various changes and modifications can be made to the claimed invention without departing from the spirit and scope thereof. Thus, for example those skilled in the art will recognize, or be able to ascertain, using no more than routine experimentation, numerous equivalents to the specific substances and procedures described herein. Such equivalents are considered to be within the scope of this invention, and are covered by the following claims.

The foregoing description has been presented only for the purposes of illustration and is not intended to limit the invention to the precise form disclosed, but by the claims appended hereto.

What is claimed is:

1. A gelatin capsule comprising a fill and a gelatin shell, wherein the gelatin shell comprises an amino-acid moiety cross linking inhibitor, and wherein the fill comprises a cross-linking inhibitor enhancer, wherein the enhancer is a carboxylic acid ester in an amount of from 0.01 to 10% (w/w) based on the weight of the fill, and wherein the gelatin capsule is adapted for oral administration.

2. The gelatin capsule of claim 1, wherein the amino acid moiety cross linking inhibitor is selected from acetylcysteine, glycine, tryptophan, lysine, leucine, threonine, aspartic acid, glutamic acid, asparagin, glutamine, arginine, cysteine, phenylalanine, tyrosine, histidine, valine, alanine, isoleucine, ormthine, p-aminobenzoic acid and nicotinic acid, or their salts.

3. The gelatin capsule of claim 1, wherein the amino-acid moiety cross linking inhibitor is in the shell in an amount of from 0.1 to 10% by weight, based on dry matter.

4. The gelatin capsule of claim 1, wherein the cross-linking inhibitor enhancer is also contained in the gelatin shell.

5. The gelatin capsule of claim 1, wherein the cross-linking inhibitor enhancer is selected from tocopherol acetate, tocopherol succinate, and d-alpha tocopheryl polyethylene glycol succinate (TPGS).

6. The gelatin capsule of claim 1, which is made via a manufacturing process using a lubricant oil containing the enhancer.

7. The gelatin capsule of claim 1, wherein said fill further comprises at least one active pharmaceutical agent.

8. The gelatin capsule of claim 7, wherein said active pharmaceutical agent is a taxane.

9. The gelatin capsule of claim 7, wherein said active pharmaceutical agent comprises an inhibitor of cytochrome 450.

10. The gelatin capsule of claim 9, wherein the inhibitor of cytochrome 450 is a cyclosporine.

11. The gelatin capsule of claim 1, wherein said amino-acid moiety cross linking inhibitor comprises glycine.

12. The gelatin capsule of claim 1, wherein said fill further comprises at least one pharmaceutically acceptable excipient which is a water-miscible liquid, a mixture of mono-, di- and triglycerides, a mixture of esters of fatty acids and polyglycerols (N=1-10), monosaccharides, disaccharides, oligosaccharides, polysaccharides, and tensides.

13. The gelatin capsule of claim 12, wherein said water-miscible liquid comprises a polyethylene glycol, a non-ionogenic surface active agent, a lower alcohol, or a mixture thereof.

14. The gelatin capsule of claim 12, wherein said tensides comprise a mixture of polyethoxylated vegetable or animal oils, polyethylene glycols, and lecithins.

15. The gelation capsule of claim 3, wherein the amount of the amino-acid moiety cross linking inhibitor in the shell is from 0.2% to 5% by weight.

16. The gelatin capsule of claim 5, wherein the amino acid moiety cross linking inhibitor is glycine.

17. The gelatin capsule of claim 1, wherein said amino-acid moiety cross linking inhibitor comprises alanine.

18. The gelatin capsule of claim 1, wherein said amino-acid moiety cross linking inhibitor comprises lysine.

19. The gelatin capsule of claim 1, wherein the gelatin capsule is adapted for oral administration in a human.

* * * * *